(12) United States Patent
Archie et al.

(10) Patent No.: US 7,791,723 B2
(45) Date of Patent: Sep. 7, 2010

(54) OPTICAL MEASUREMENT USING FIXED POLARIZER

(75) Inventors: Charles N. Archie, Granite Springs, NY (US); Matthew J. Sendelbach, Fishkill, NY (US); Shahin Zangooie, Hopewell Junction, NY (US)

(73) Assignee: International Business Machines Corporation, Armonk, NY (US)

( * ) Notice: Subject to any disclaimer, the term of this patent is extended or adjusted under 35 U.S.C. 154(b) by 282 days.

(21) Appl. No.: 12/017,151

(22) Filed: Jan. 21, 2008

(65) Prior Publication Data

US 2009/0185168 A1 Jul. 23, 2009

(51) Int. Cl.
*G01N 4/00* (2006.01)

(52) U.S. Cl. .................................. 356/364

(58) Field of Classification Search ............... None
See application file for complete search history.

(56) References Cited

U.S. PATENT DOCUMENTS

| | | | |
|---|---|---|---|
| 5,042,951 A | 8/1991 | Gold et al. | |
| 5,596,411 A | 1/1997 | Fanton et al. | |
| 5,877,859 A | 3/1999 | Aspnes et al. | |
| 6,429,943 B1 | 8/2002 | Opsal et al. | |
| 6,515,746 B2 | 2/2003 | Opsal et al. | |
| 6,678,046 B2 | 1/2004 | Opsal | |
| 2002/0015146 A1* | 2/2002 | Meeks et al. | 356/73 |
| 2007/0273858 A1* | 11/2007 | Nagasaka | 355/67 |

OTHER PUBLICATIONS

Unknown, "Metrology", International Technology Roadmap for Semiconductors 2006 Update, 20 pages.

Taylor et al., "Guidelines for Evaluating and Expressing the Uncertainty of NIST Measurement Results," United States Department of Commerce Technology Administration, National Institute of Standards and Technology, NIST Technical Note 1297 1994 Edition, Sep. 1994, 25 pages.

\* cited by examiner

*Primary Examiner*—Tu T Nguyen
(74) *Attorney, Agent, or Firm*—Ian MacKinnon; Hoffman Warnick LLC

(57) ABSTRACT

Optical measurement method and systems employing a fixed polarizer are disclosed. In one embodiment, the method includes providing at least one optical detection system having a fixed polarizer having a first type polarization; providing a first target on a substrate and a second target on the substrate; optically measuring the first target and the second target using the at least one optical detection system with the first target being positioned at a right angle relative to the second target to obtain a first measurement with the first type polarization and a second measurement with a second type-equivalent polarization; and combining the first measurement and the second measurement to obtain the optical measurement.

18 Claims, 7 Drawing Sheets

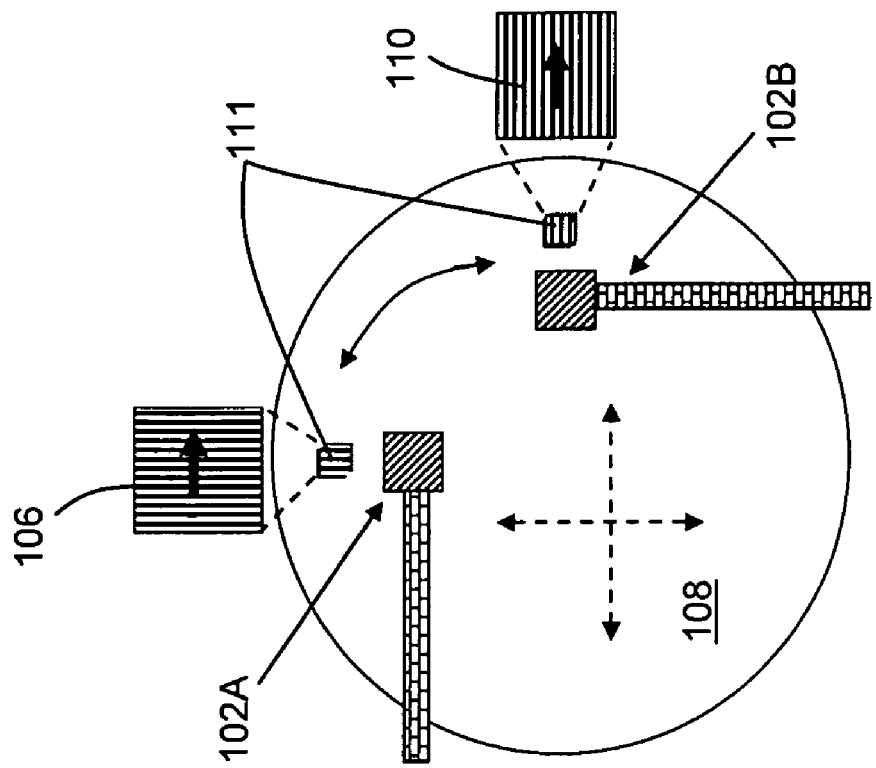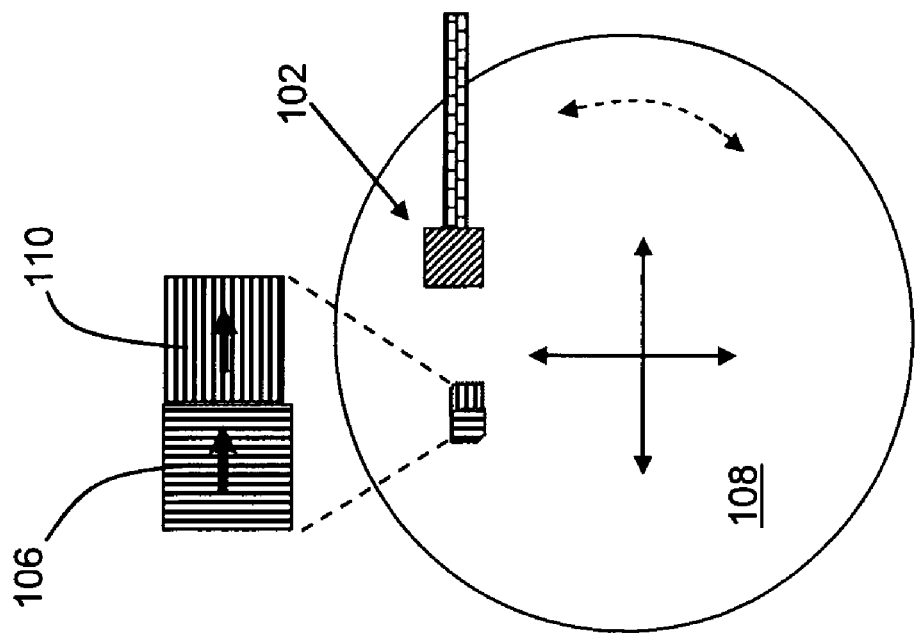

OPTICAL MEASUREMENT USING FIXED POLARIZER

BACKGROUND

1. Technical Field

The disclosure relates generally to metrology, and more particularly, to a method and systems for optical measurement.

2. Background Art

Optical metrology is an integral part of semiconductor research and development, and manufacturing. For example, semiconductor dimensions that may require measurements via optical metrology tools include: thickness, critical dimension (CD), sidewall angle (SWA), doping, reactive ion etching (RIE) lag, etch bias, etc., Optical metrology tools may also be used to verify lithography focus and provide exposure feedback. The benefits include non-contact measurement capability with little or no risk of damage or contamination to the sample.

One form of optical metrology is scatterometry, which generally requires a target grating along with an optical system which collects optical spectra for analysis. Targets 10, as illustrated in FIGS. 1A-B, usually consist of a 50 µm×50 µm grating 12 with a series of lines 14 and adjacent spaces (FIG. 1B simplified compared to FIG. 1A for clarity). The optical systems (not shown) used to illuminate grating 12 and collect the optical spectra generally utilize different versions of ellipsometry and/or reflectometry. As shown in FIG. 2A, ellipsometry uses an incident light beam 15 illuminating target 10 at an angle not normal to a wafer surface 16. This results in a spot which resembles an ellipse 18. As shown in FIG. 2B, reflectometry uses an incident light beam 19 illuminating target 10 at an angle normal to wafer surface 20, resulting in a substantially circular spot 22. Reflectometry often uses specific optical components, such as a polarizer (not shown), which makes the measurement sensitive to grating 10 direction. Regardless of which type of optical system is utilized the reflected beam contains the information which must be analyzed and processed to compute the desired measurement parameters using an optical model specifically created for the target being measured.

Each technique employs a variety of optics arrangements utilizing rotating and/or fixed polarizers and compensators. One problem with moving components, however, is that they oftentimes suffer from frequent mechanical and alignment problems.

SUMMARY

Optical measurement method and systems employing a fixed polarizer are disclosed. In one embodiment, the method includes providing at least one optical detection system having a fixed polarizer having a first type polarization; providing a first target on a substrate and a second target on the substrate; optically measuring the first target and the second target using the at least one optical detection system with the first target being positioned at a right angle relative to the second target to obtain a first measurement with the first type polarization and a second measurement with a second type-equivalent polarization; and combining the first measurement and the second measurement to obtain the optical measurement.

A first aspect of the disclosure provides a method of performing an optical measurement, the method comprising: providing at least one optical detection system having a fixed polarizer having a first type polarization; providing a first target on a substrate and a second target on the substrate; optically measuring the first target and the second target using the at least one optical detection system with the first target being positioned at a right angle relative to the second target to obtain a first measurement with the first type polarization and a second measurement with a second type-equivalent polarization; and combining the first measurement and the second measurement to obtain the optical measurement.

A second aspect of the disclosure provides an optical measurement system comprising: at least one optical detection system having a fixed polarizer having a first type polarization for measuring a first target on a substrate and a second target on the substrate; a positioner for moving the substrate between a first measurement position for the first target and a second measurement position for the second target at which the second target is at a right angle relative to the first target to obtain a first measurement with the first type polarization and a second measurement with a second type-equivalent polarization; and a calculator for combining the first measurement and the second measurement to obtain the optical measurement.

A third aspect of the disclosure provides an optical measurement system comprising: a plurality of optical detection systems having a shared fixed polarizer having a first type polarization for measuring a first target on a substrate and a second target on the substrate; a positioner for moving the substrate between a first measurement position for the first target and a second measurement position for the second target at which the second target is at a right angle relative to the first target to obtain a first measurement with the first type polarization and a second measurement with a second type-equivalent polarization; and a calculator for averaging the first measurement and the second measurement to obtain the optical measurement.

The illustrative aspects of the present disclosure are designed to solve the problems herein described and/or other problems not discussed.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which:

FIG. 4 shows one embodiment of a substrate according to the disclosure.

FIG. 5 shows another embodiment of a substrate according to the disclosure.

It is noted that the drawings of the disclosure are not to scale. The drawings are intended to depict only typical aspects of the disclosure, and therefore should not be considered as limiting the scope of the disclosure. In the drawings, like numbering represents like elements between the drawings.

DETAILED DESCRIPTION

Optical measurement method and systems will be described herein to realize high speed and high information content scatterometry measurements. The approaches described herein are also usable for a large number of thin film measurement applications. For convenience, the following illustrations often use high numerical aperture (NA) lens angle resolved schematics. However, the ideas can be easily generalized to other techniques such as oblique incidence ellipsometry.

Figure 1B:
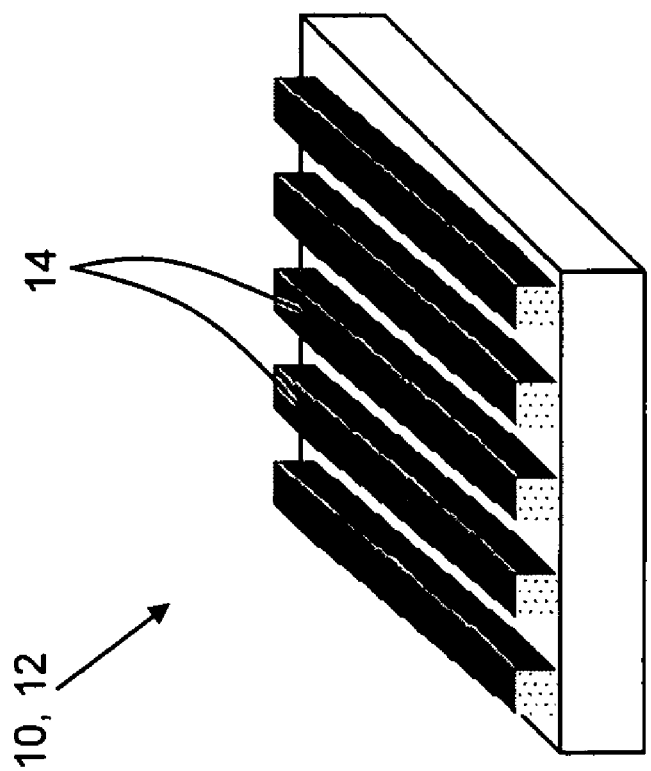
FIGS. 1A-B shows periodic line/space targets which are measured by scatterometry.
Figure 1A:
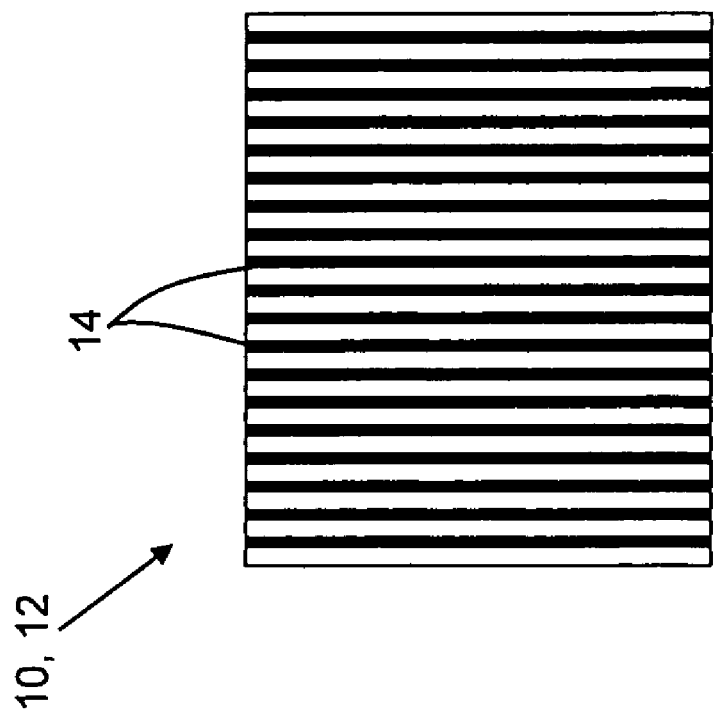
Figure 2A:
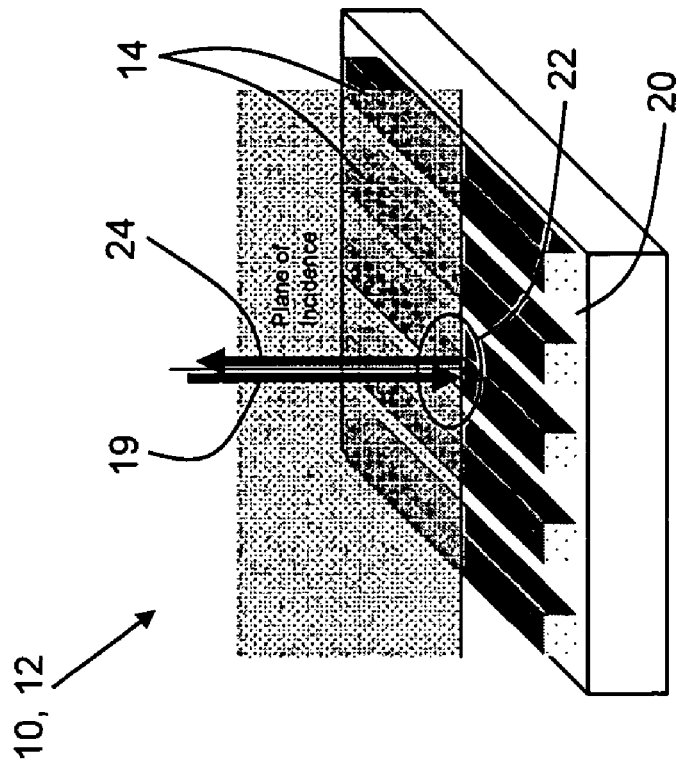
FIGS. 2A-B show a conventional ellipsometry and reflectometry techniques.
Figure 2B:
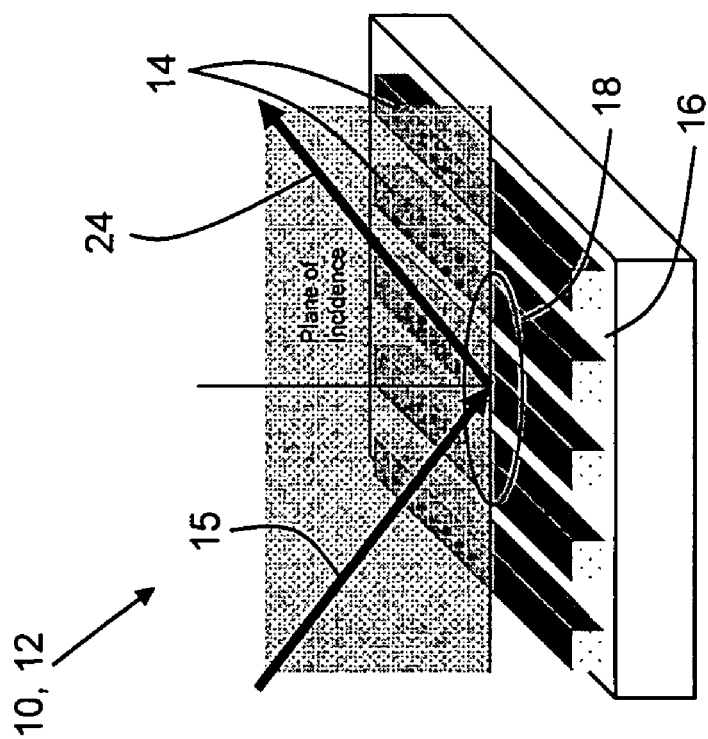
Figure 3:
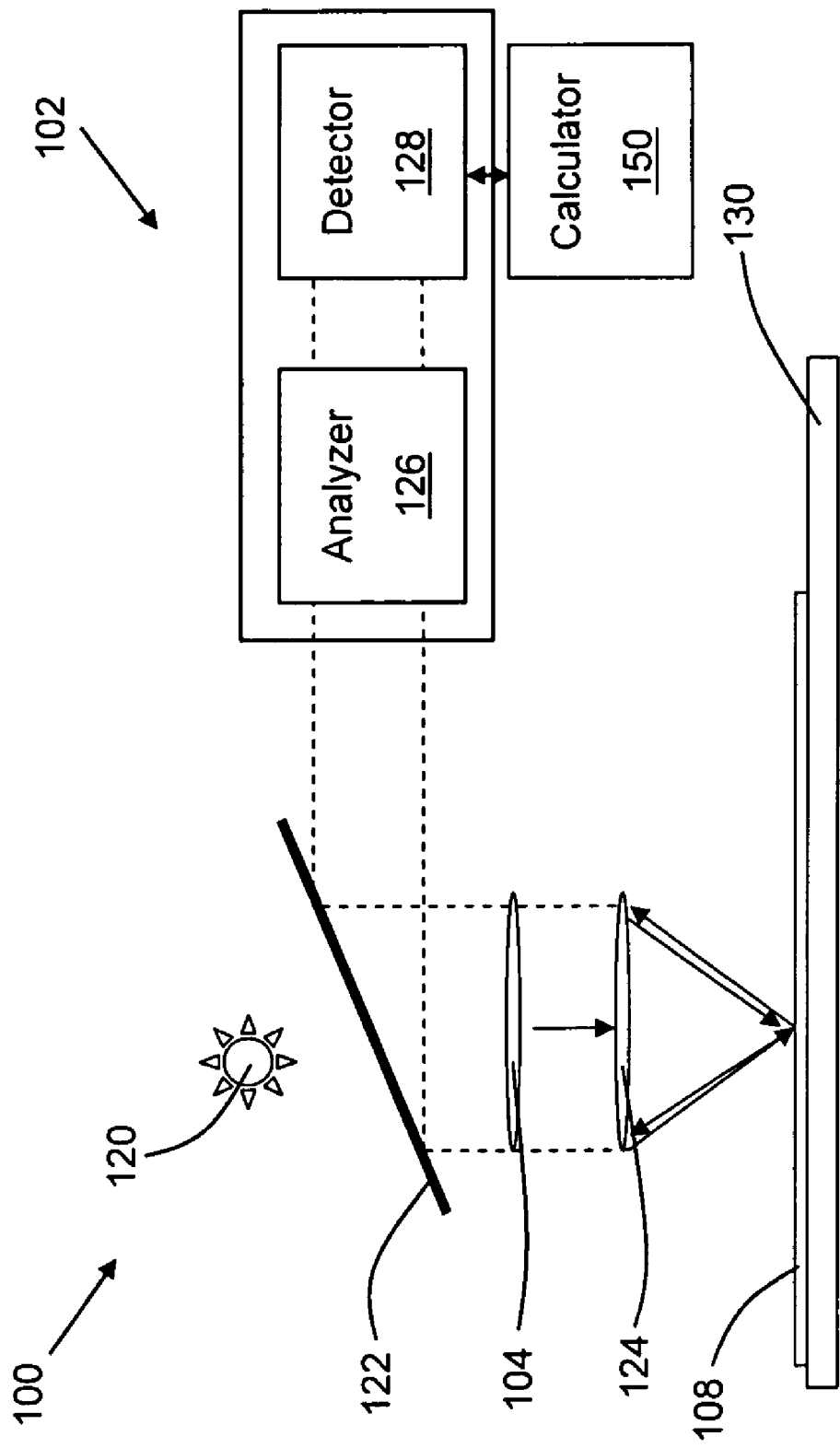
FIG. 3 shows one embodiment of an optical measurement system 100 according to the disclosure.

FIG. 3 shows one embodiment of an optical measurement system 100 according to the disclosure. System 100 includes at least one optical detection system (ODS) 102 having a fixed polarizer 104 having a first type polarization (e.g., p-polarized or s-polarized) for measuring a first target 106 (FIGS. 4-5) on a substrate 108 and a second target 110 (FIGS. 4-5) on substrate 108. Substrate 108 may include, for example, a semiconductor wafer having targets 106, 110 thereon. Targets 106, 110, in one embodiment, may include a number of parallel, raised, line structures (forming a grating) to be measured, and are substantially identical. However, the teachings of the invention are not limited to this type substrate or these type targets. In particular, the targets do not necessarily have to be substantially identical. As shown in FIG. 4, in one embodiment, targets 106, 110 are placed adjacent to one another such that one target is positioned at a right angle relative to the other target on the substrate to, for example, avoid/minimize impacts/errors caused by possible microstructural non-uniformities across substrate (across wafer) 108. As used herein, "at a right angle" typically means at exactly 90°, but may also include any known offsets from exactly 90° that are compensated for in the analysis. Alternatively, as shown in FIG. 5, a single target 111 may be used and the substrate 108 rotated for measurement by different ODSs.

Returning to FIG. 3, fixed polarizer 104 is positioned between a light source 120 and a beam splitting mirror 122 and a high numerical aperture (NA) lens 124. ODS 102 may further include a conventional analyzer 126 and detector 128. Fixed polarizer 104 can be set to generate either s-polarized incident light or p-polarized incident light. "s-polarized incident light" is a component of a light beam which is normal to the plane of incidence of the light beam, and "p-polarized incident light" is a component of a light beam that is parallel to the plane of incidence of the light beam. Simple applications specific sensitivity analysis would be sufficient to determine appropriate polarization setup prior to each measurement.

A positioner 130 (FIG. 3) is configured for moving substrate 108 between a first measurement position, as shown in FIGS. 4 and 5, for first target 106 and a second measurement position for second target 110 at which the second target is at a right angle (i.e., turned ~90°) relative to the first target to obtain a first measurement with the first type polarization and a second measurement with a second type-equivalent polarization. That is, if both polarization states are required, an existing s- or p-fixed polarizer 104 is used to measure equivalent p- or s-polarized measurements, respectively, on a closely situated sister target with grating orientation designed at +/−90° offset. If the fixed polarizer 104 (polarization) is s-polarized, the type-equivalent polarization is p-equivalent polarized; if fixed polarizer 104 (polarization) is p-polarized, and the type-equivalent polarization is s-equivalent polarized. In terms of substrate 108, as shown in FIG. 4, positioner 130 would move substrate in lateral directions as shown by the arrows between a first measurement position and a second measurement position. Positioner 130 may also rotate substrate 108, as shown by phantom arrow, between first measurement and a second measurement position, if necessary. In terms of substrate 108, as shown in FIG. 5, positioner 130 would rotate substrate 108 (+/−90°) as shown by the arrow between a first measurement position and a second measurement position for single target 111, i.e., single target becomes the first target and the second target via the rotation of substrate 108. Positioner 130, in FIG. 5, may also move substrate 108 in lateral X, Y directions as shown by the phantom arrows, if necessary. In this manner, equivalent complementary measurements for s- and p-polarizations can be attained without changing the polarization of fixed polarizer 104. That is, fixed polarizer 104 is not moved during measurements—target(s) 106, 110, 111 are moved to orthogonal positions to attain equivalent s-polarized and p-equivalent polarized (or p-polarized and s-equivalent polarized) measurements.

Figure 6:
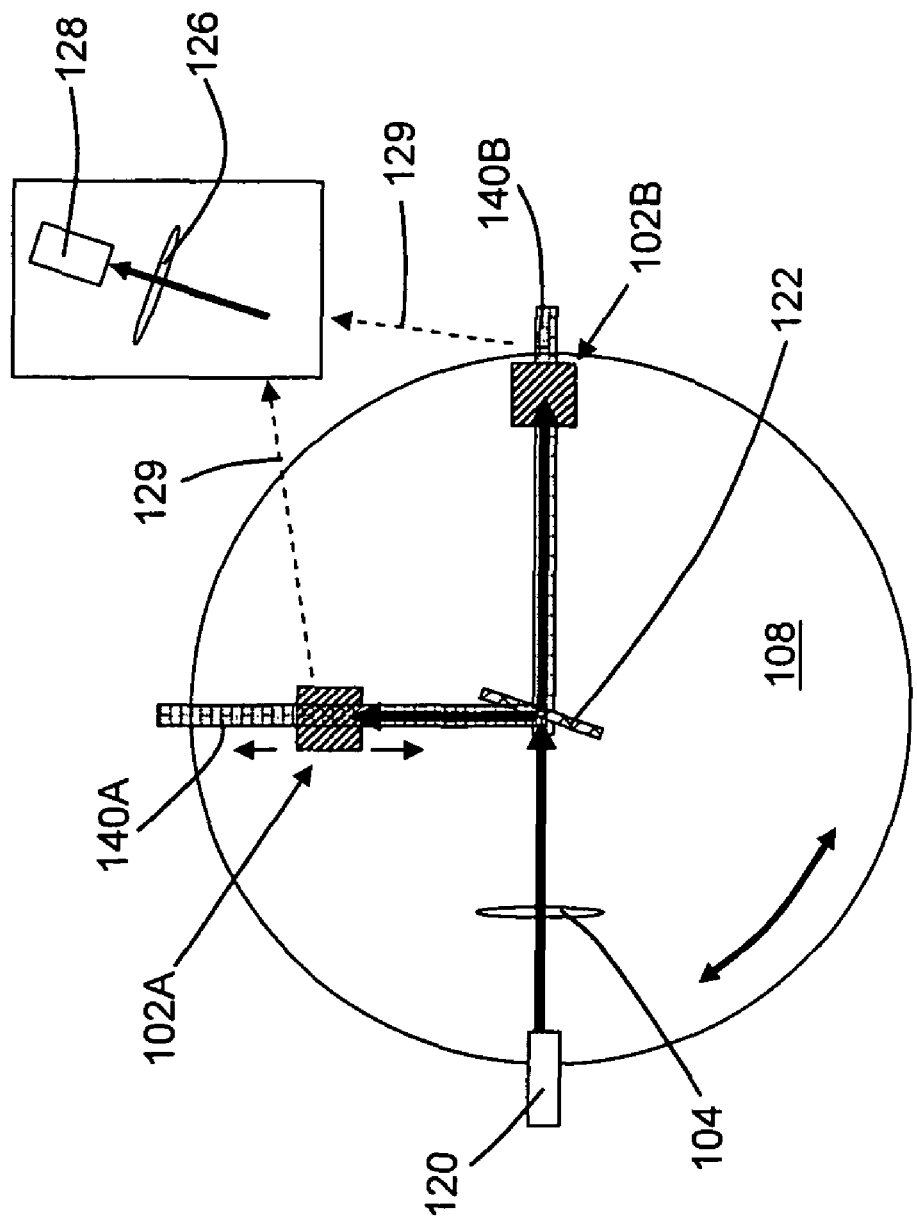
FIG. 6 shows embodiments of an optical measurement system according to the disclosure.
Figure 7:
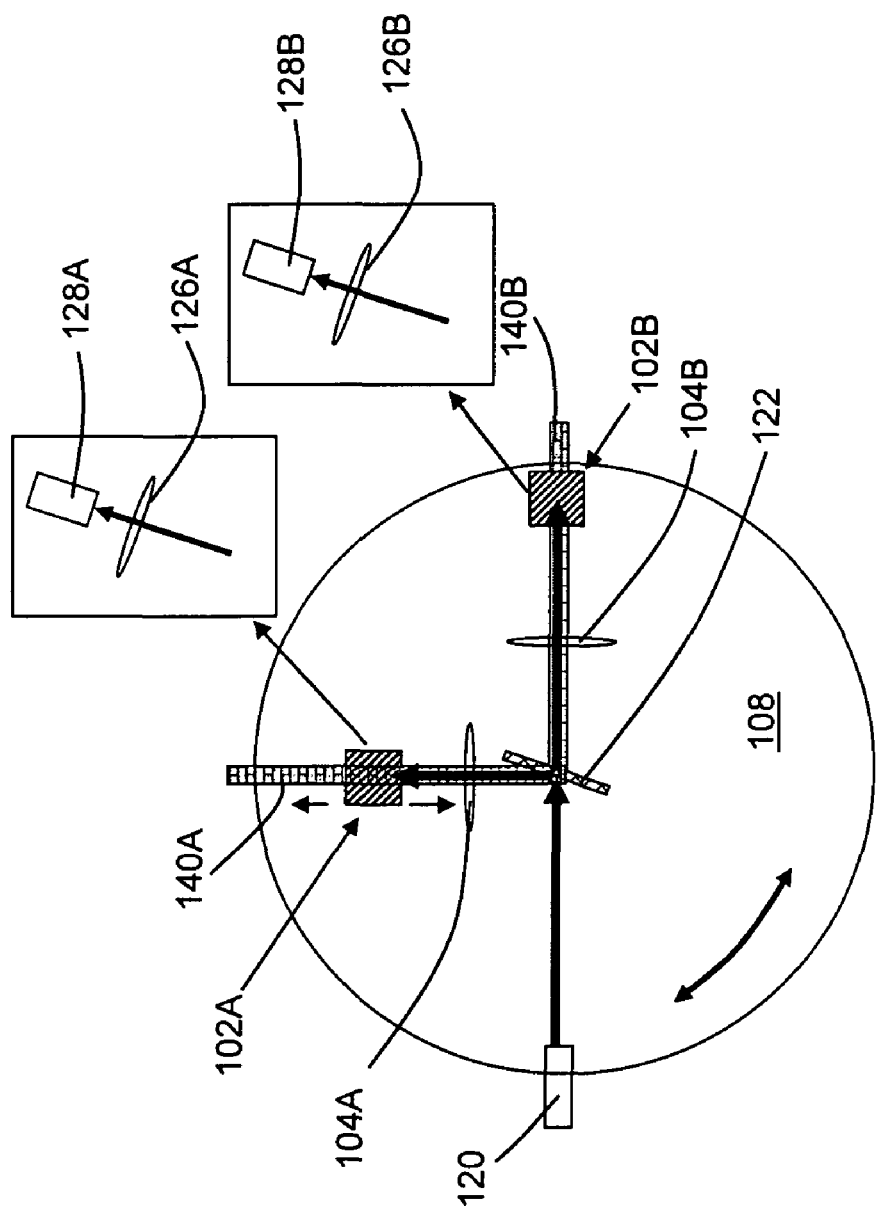
FIG. 7 shows other embodiments of an optical measurement system according to the disclosure.

Referring to FIGS. 6-7, in one embodiment, a number of optical detection systems (ODS) 102A-B may be employed, such that a first ODS 102A and a second ODS 102B can simultaneously measure first target 106 and second target 110 (under ODSs 102A-102B in FIG. 6). In this arrangement, throughput of the system may be increased. For example, ODSs 102A-B may be able to measure different structural targets with different structural characteristics simultaneously, which improves throughput. In one embodiment, ODS 102A may use a differently polarized fixed polarizer 104 (e.g., s-polarized) compared to ODS 102B (e.g., p-polarized). As shown in FIG. 6, first ODS 102A and second ODS 102B may share certain components such as fixed polarizer 104, beam splitting mirror 122, analyzer 126 and detector 128. In FIG. 6, a compensator (not shown) may be placed ahead of beam splitting mirror 122. This arrangement may also require use of optical fibers, but may allow for improved matching performance. The reflected light from split channels 129 can be redirected back to detector 128. One beam would be blocked at any given time, but the blocking gates (not shown) could be activated while the stage is moving from one target 110 (grating orientation) to the other target 106 so it would not impact move/acquire/measure (MAM) time, but allow for a better matched system. Alternatively, as shown in FIG. 7, each ODS 102A, 102B may be a standalone system having, for example, respective fixed polarizers 104A, 104B, analyzers 126A, 126B, and detectors 128A, 128B. In any event, first and second ODS 102A, 102B may be movable relative to substrate 108 by, for example, a respective mounting rail or robotic arm 140A, 140B. However, a fixed position for ODS(s) 102A, 102B may also be employed in some instances.

The FIGS. 6-7 arrangements allow for, for example, simultaneous s-polarized or p-polarized measurements on two similar or different targets 106, 110 (FIG. 6), or simultaneous s-polarized and/or p-polarized measurements on two similar or different targets 106, 110 (FIG. 6 or 7). In FIGS. 6-7, ODS(s) 102A-B can individually function in active focus or freeze focus modes. Normalization can be performed using a shared reference chip and optical path (not shown). The polarization states and measurement strategy involving the stage and ODS(s) 102 motions are part of a measurement recipe and are computer controlled. Optimization software may be needed to decide the most optimum measurement strategy involving complex multiple structure/target measurements.

System 100 may be employed to use either s-polarized or p-polarized spectra. The spectral choice can be made based on an initial sensitivity and accuracy analysis. The accuracy control may be realized using techniques such as a total measurement uncertainty (TMU) routine. Furthermore, the parameter sensitivity may be controlled using dynamic and/or static precision measurements.

In other cases, however, system 100 (FIG. 3) may employ different polarization states (s- and p-polarized spectra), which may provide different level of sensitivity to profile characteristics. For example, s-polarized light may provide significant sensitivity to side wall angle and critical dimension (CD), whereas p-polarized light may give significant sensitivity to trench depth. It is therefore oftentimes beneficial to combine both the s-polarized and p-polarized equivalent data (or p-polarized and s-polarized equivalent data) to maximize measurement sensitivity. (Note again, that s-polarized equivalent measurement is done using p-polarized light on the +/−90 degrees oriented sister target and the p-polarized equivalent data is collected using s-polarized light and the +/−90 degrees oriented target). To this end, returning to FIG. 3, system 100 may also include a calculator 150 for combining a first measurement (using s- or p-polarized light) and a second measurement (using p-equivalent or s-equivalent light) to obtain an optical measurement, i.e., a measurement result, for targets 106, 110 (FIGS. 4-5). That is, in one embodiment, first target 106 and second target 110 are optically measured using ODS(s) 102 with first target 106 being positioned at a right angle relative to second target 110 to obtain a first measurement with the first type polarization and a second measurement with a second type-equivalent polarization.

Figure 8:
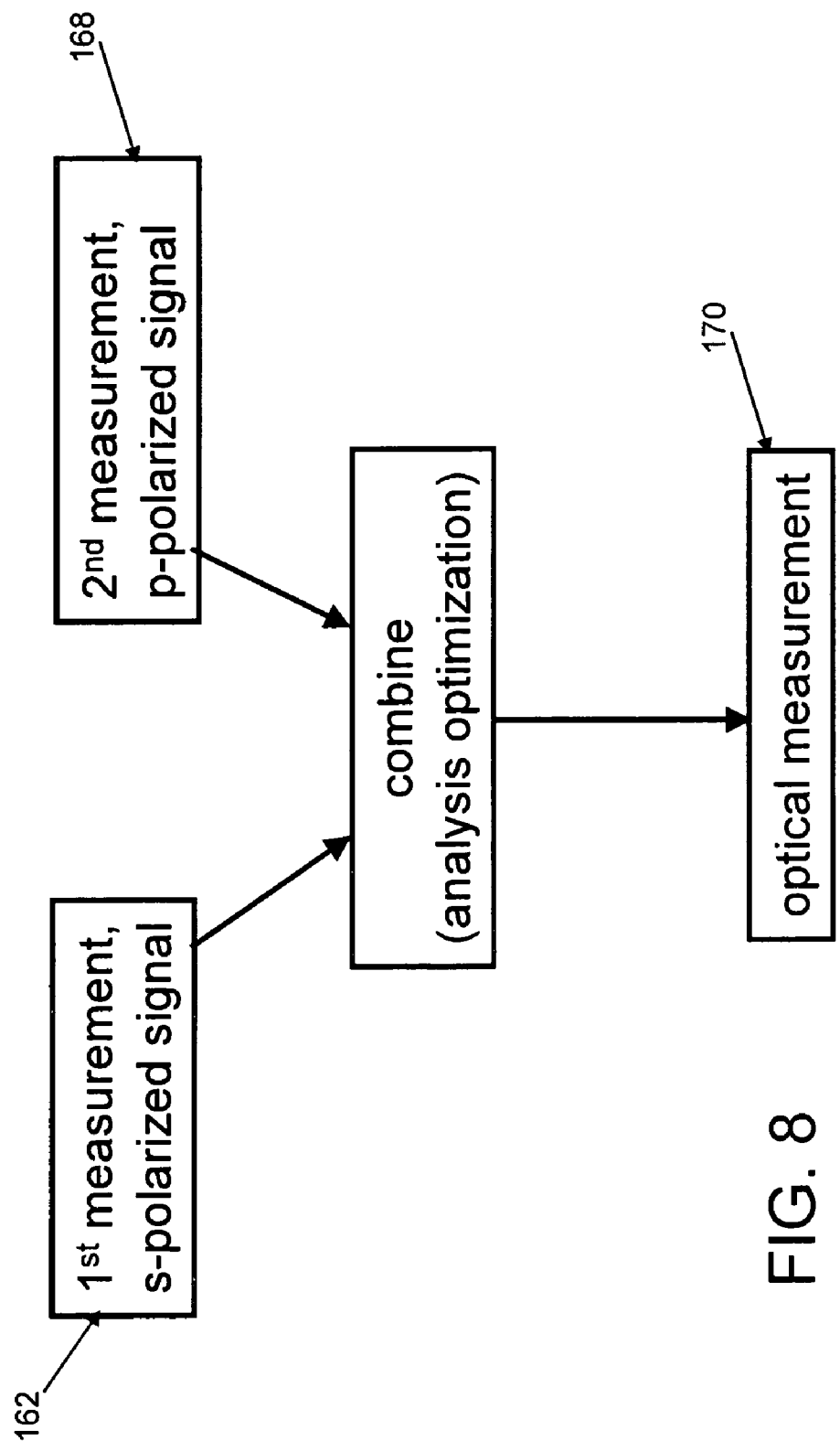
FIG. 8 shows a schematic illustrating combining of measurements.

In one embodiment, calculator 150 combines the first and second measurements by any now known or later developed combinatorial technique. As shown in FIG. 8, a first measurement 162 of a first target 106 (FIGS. 4-5) and a second measurement 168 of a second target 110 (FIGS. 4-5), which can be s-polarized and p-polarized, respectively, can be made combined (perhaps with analysis optimization) by calculator 150 (FIG. 3) to obtain a final optical measurement 170. In one example, calculator 150 may simply average first measurement 162 and second measurement 168 to determine the optical measurement. In one embodiment, calculator 150 may perform a measurement uncertainty analysis optimization of first measurement 162 and second measurement 168 to determine an optimized weighting value for the first measurement and the second measurement. Measurement uncertainty analysis may include any technique as described in, for example, Taylor, B. N. & Kuyaft C. E., "Guidelines for Evaluating and Expressing the Uncertainty of NIST Measurement Results", NIST Technical Note 1297, 1994 Edition. The measurement uncertainty would be implemented as part of a feedback loop to improve the accuracy of the optical measurement. In another embodiment, the measurement uncertainty minimization may include using any component of measurement uncertainty: repeatability, reproducibility, precision, accuracy, matching, total measurement uncertainty (TMU), and fleet measurement precision (FMP).

Calculator 150 can comprise any general purpose computing article of manufacture capable of executing computer program code installed by a user (e.g., a personal computer, server, handheld device, etc.). However, it is understood that calculator 150 is only representative of various possible equivalent computing devices that may perform the various process steps of the disclosure. To this extent, in other embodiments, calculator 150 can comprise any specific purpose computing article of manufacture comprising hardware and/or computer program code for performing specific functions, any computing article of manufacture that comprises a combination of specific purpose and general purpose hardware/software, or the like. In each case, the program code and hardware can be created using standard programming and engineering techniques, respectively.

As discussed herein, various systems and components are described as "obtaining" data (e.g., calculator 150, etc.). It is understood that the corresponding data can be obtained using any solution. For example, the corresponding system/component can generate and/or be used to generate the data, retrieve the data from one or more data stores (e.g., a database), receive the data from another system/component, and/or the like. When the data is not generated by the particular system/component, it is understood that another system/component can be implemented apart from the system/component shown, which generates the data and provides it to the system/component and/or stores the data for access by the system/component.

While shown and described herein as a method and system for optical measurement, it is understood that the disclosure further provides various alternative embodiments. That is, parts of the disclosure, e.g., calculator 150, can take the form of an entirely hardware embodiment, an entirely software embodiment or an embodiment containing both hardware and software elements. In a preferred embodiment, the calculator 150 is implemented in software, which includes but is not limited to firmware, resident software, microcode, etc. In one embodiment, calculator 150 can take the form of a computer program product accessible from a computer-usable or computer-readable medium providing program code for use by or in connection with a computer or any instruction execution system, which when executed, enables a computer infrastructure to perform the optical measurement determination and related data processing described herein. For the purposes of this description, a computer-usable or computer readable medium can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, such as magnetic tape, a removable computer diskette, a random access memory (RAM), a read-only memory (ROM), a tape, a rigid magnetic disk and an optical disk. Current examples of optical disks include compact disk-read only memory (CD-ROM), compact disk-read/write (CD-R/W) and DVD.

As used herein, it is understood that the terms "program code" and "computer program code" are synonymous and mean any expression, in any language, code or notation, of a set of instructions that cause a computing device having an information processing capability to perform a particular function either directly or after any combination of the following: (a) conversion to another language, code or notation; (b) reproduction in a different material form; and/or (c) decompression. To this extent, program code can be embodied as one or more types of program products, such as an application/software program, component software/a library of functions, an operating system, a basic I/O system/driver for a particular computing and/or I/O device, and the like.

The foregoing description of various aspects of the disclosure has been presented for purposes of illustration and description. It is not intended to be exhaustive or to limit the disclosure to the precise form disclosed, and obviously, many modifications and variations are possible. Such modifications and variations that may be apparent to a person skilled in the art are intended to be included within the scope of the disclosure as defined by the accompanying claims.

What is claimed is:

1. A method of performing an optical measurement, the method comprising:
   providing at least one optical detection system having a fixed polarizer having a first type polarization;
   providing a first target on a substrate and a second target on the substrate, wherein the first target and the second target each have parallel gratings, wherein the first target is adjacent to the second target, and wherein the parallel gratings of the second target are positioned at a right angle relative to the parallel gratings of the first target;
   optically measuring the first target and the second target using the at least one optical detection system to obtain a first measurement with the first type polarization and a second measurement with a second type-equivalent polarization; and
   combining the first measurement and the second measurement to obtain the optical measurement.

2. The method of claim 1, wherein the providing includes providing the substrate with a single target and further comprising rotating the substrate such that during the optical measuring of the single target, the single target provides the first target and the second target by rotation to positions at a right angle relative to one another.

3. The method of claim 2, wherein the at least one optical detection system (ODS) includes a first ODS and a second ODS, and wherein the optical measuring includes simultaneously measuring the first target and the second target using the first ODS and the second ODS.

4. The method of claim 3, wherein the first ODS and the second ODS share the fixed polarizer.

5. The method of claim 3, wherein the first ODS and the second ODS each have a fixed polarizer.

6. The method of claim 1, wherein the first type polarization is s-polarized, and the second type-equivalent polarization is p-equivalent polarized.

7. The method of claim 1, wherein the first target and the second target are substantially identical.

8. The method of claim 1, wherein the combining includes averaging the first measurement and the second measurement to determine the optical measurement.

9. The method of claim 8, further comprising performing a measurement uncertainty analysis of the first measurement and the second measurement to determine an optimized weighting value for the first measurement and the second measurement.

10. An optical measurement system comprising:
    at least one optical detection system having a fixed polarizer having a first type polarization for measuring a first target on a substrate and a second target on the substrate;
    a positioner for moving the substrate between a first measurement position for the first target and a second measurement position for the second target at which the second target is at a right angle relative to the first target to obtain a first measurement with the first type polarization and a second measurement with a second type-equivalent polarization, wherein the first target and the second target each have parallel gratings, wherein the first target is adjacent to the second target, and wherein the parallel gratings of the second target are positioned at a right angle relative to the parallel gratings of the first target; and
    a calculator for combining the first measurement and the second measurement to obtain the optical measurement.

11. The system of claim 10, wherein the substrate includes a single target, wherein the positioner rotates the substrate between the first measurement position to measure the single target as the first target and the second measurement position to measure the single target as the second target.

12. The system of claim 11, wherein the at least one optical detection system (ODS) includes a first ODS and a second ODS, and wherein the first and second ODS simultaneously measure the first target and the second target.

13. The system of claim 12, wherein the first ODS and the second ODS share the fixed polarizer.

14. The system of claim 10, wherein the calculator averages the first measurement and the second measurement to determine the optical measurement.

15. The system of claim 14, wherein the calculator performs a measurement uncertainty analysis of the first measurement and the second measurement to determine an optimized weighting value for the first measurement and the second measurement.

16. The system of claim 10, wherein the first type polarization is s-polarized, and the second type-equivalent polarization is p-equivalent polarized.

17. The system of claim 10, wherein the first target and the second target are substantially identical.

18. An optical measurement system comprising:
    a plurality of optical detection systems having a shared fixed polarizer having a first type polarization for measuring a first target on a substrate and a second target on the substrate;
    a positioner for moving the substrate between a first measurement position for the first target and a second measurement position for the second target at which the second target is at a right angle relative to the first target to obtain a first measurement with the first type polarization and a second measurement with a second type-equivalent polarization, wherein the first target and the second target each have parallel gratings, wherein the first target is adjacent to the second target, and wherein the parallel gratings of the second target are positioned at a right angle relative to the parallel gratings of the first target; and
    a calculator for averaging the first measurement and the second measurement to obtain the optical measurement.

* * * * *